(12) United States Patent
Porubanova et al.

(10) Patent No.: US 12,066,637 B1
(45) Date of Patent: Aug. 20, 2024

(54) ADJUSTING IPD SETTINGS TO MATCH INTEROCULAR DISTANCE IN EXTENDED REALITY DEVICES

(71) Applicant: Microsoft Technology Licensing, LLC, Redmond, WA (US)

(72) Inventors: Michaela Porubanova, Seattle, WA (US); Gregory Michael Link, Charlotte, NC (US); Mohammadamin Eftekhar, Mercer Island, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/210,578

(22) Filed: Jun. 15, 2023

(51) Int. Cl.
*G02B 27/01* (2006.01)
(52) U.S. Cl.
CPC ..... *G02B 27/0179* (2013.01); *G02B 27/0103* (2013.01); *G02B 2027/0174* (2013.01); *G02B 2027/0187* (2013.01)

(58) Field of Classification Search
None
See application file for complete search history.

(56) References Cited

U.S. PATENT DOCUMENTS

| | | | | |
|---|---|---|---|---|
| 2016/0349510 | A1* | 12/2016 | Miller | H04N 13/398 |
| 2016/0349837 | A1* | 12/2016 | Miller | H04N 13/344 |
| 2017/0309071 | A1 | 10/2017 | Benko et al. | |
| 2019/0238818 | A1 | 8/2019 | Held | |
| 2019/0295323 | A1 | 9/2019 | Gutierrez et al. | |

OTHER PUBLICATIONS

Non-Final Office Action mailed on Jan. 19, 2024, in U.S. Appl. No. 18/210,576, 10 pages.
U.S. Appl. No. 18/210,572, filed Jun. 15, 2023.
U.S. Appl. No. 18/210,576, filed Jun. 15, 2023.
U.S. Appl. No. 18/210,577, filed Jun. 15, 2023.
U.S. Appl. No. 18/651,406, filed Apr. 30, 2024.
Notice of Allowance mailed on May 9, 2024, in U.S. Appl. No. 18/210,576, 7 pages.

* cited by examiner

*Primary Examiner* — Parul H Gupta
(74) *Attorney, Agent, or Firm* — Workman Nydegger

(57) ABSTRACT

Techniques for facilitating calibration of an IPD for an ER system are disclosed. A current IPD setting for the ER system is determined. An object in a scene is selected. A first distance between the ER system and the object is determined. A hologram is generated, where this hologram includes at least one boundary region that corresponds to at least one boundary region of the object. The hologram is displayed in the scene. The hologram is displayed based on the current IPD setting for the ER system. User input adjusts the current IPD setting such that a new IPD setting is provided to the ER system. The hologram is displayed in the scene based on the new IPD setting. Based on the new IPD setting, the hologram is caused to align with the object, thereby calibrating the IPD setting.

20 Claims, 15 Drawing Sheets

ADJUSTING IPD SETTINGS TO MATCH INTEROCULAR DISTANCE IN EXTENDED REALITY DEVICES

BACKGROUND

The phrase "extended reality" (ER) is an umbrella term that collectively describes various different types of immersive platforms. Such immersive platforms include virtual reality (VR) platforms, mixed reality (MR) platforms, and augmented reality (AR) platforms.

For reference, conventional VR systems create completely immersive experiences by restricting their users' views to only virtual environments. This is often achieved through the use of a head mounted device (HMD) that completely blocks any view of the real world. With this HMD, a user can be entirely or partially immersed within an immersive environment. Conventional AR systems create an augmented reality experience by visually presenting virtual objects that are placed in the real world. Conventional MR systems also create an augmented reality experience by visually presenting virtual objects that are placed in the real world. In the context of an MR system, those virtual objects are typically able to be interacted with by the user, and those virtual objects can interact with real world objects. AR and MR platforms can also be implemented using an HMD.

Unless stated otherwise, the descriptions herein apply equally to all types of ER systems, which include MR systems, VR systems, AR systems, and/or any other similar system capable of displaying virtual content. An ER system can be used to display various different types of information to a user. Some of that information is displayed in the form of a "hologram." As used herein, the term "hologram" generally refers to virtual image content that is displayed by an ER system. In some instances, the hologram can have the appearance of being a three-dimensional (3D) object while in other instances the hologram can have the appearance of being a two-dimensional (2D) object.

Often, holograms are displayed in a manner as if they are a part of the actual physical world. For instance, a hologram of a flower vase might be displayed on a real-world table. In this scenario, the hologram can be considered as being "locked" or "anchored" to the real world. Such a hologram can be referred to as a "world-locked" hologram or a "spatially-locked" hologram that is spatially anchored to the real world. Regardless of the user's movements, a world-locked hologram will be displayed as if it was anchored or associated with the real-world. Other holograms can be locked to a particular position in the user's field of view (FOV). In any event, ER systems are able to generate numerous different types of holograms.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

In some aspects, the techniques described herein relate to an extended reality (ER) system that facilitates calibration of an interpupillary distance (IPD) setting, said ER system including: a processor system; and a storage system that stores instructions that are executable by the processor system to cause the ER system to: determine a current IPD setting for the ER system; select an object in a scene in which the ER system is operating; determine a first distance from the ER system to the object; generate a hologram including at least one boundary region that corresponds to at least one boundary region of the object; display the hologram in the scene, wherein the hologram is displayed based on the current IPD setting for the ER system, and wherein the hologram is displayed at a second distance from the ER system, the second distance being observably different than the first distance; receive user input adjusting the current IPD setting such that a new IPD setting is provided to the ER system; display the hologram in the scene at a third distance from the ER system, the third distance being observably the same as the first distance, wherein, as a result of displaying the hologram at the third distance, the at least one boundary region of the hologram aligns with the least one boundary region of the object; and cause the current IPD setting to be used for subsequent display operations of the ER system.

In some aspects, the techniques described herein relate to a method, implemented by an extended reality (ER) system, for facilitating calibration of an interpupillary distance (IPD) setting for the ER system, said method including: determining a current IPD setting for the ER system; selecting an object in a scene in which the ER system is operating; determining a first distance from the ER system to the object; generating a hologram that corresponds to the object; displaying the hologram in the scene, wherein the hologram is displayed based on the current IPD setting for the ER system, and wherein the hologram is displayed at a second distance from the ER system, the second distance being an approximation of the first distance based on the current IPD setting; receiving user input adjusting the current IPD setting such that a new IPD setting is provided to the ER system; displaying the hologram in the scene at a third distance from the ER system, the third distance also being an approximation of the first distance based on the new IPD setting; and causing the current IPD setting to be used for subsequent display operations of the ER system.

In some aspects, the techniques described herein relate to a method, implemented by an extended reality (ER) system, for facilitating calibration of an interpupillary distance (IPD) for the ER system, said method including: determining a current IPD setting for the ER system; selecting an object in a scene in which the ER system is operating; determining a first distance from the ER system to the object; generating a hologram including at least one boundary region that corresponds to at least one boundary region of the object; displaying the hologram in the scene, wherein the hologram is displayed based on the current IPD setting for the ER system, and wherein the hologram is displayed at a second distance from the ER system, the second distance being an approximation of the first distance based on the current IPD setting; receiving user input adjusting the current IPD setting such that a new IPD setting is provided to the ER system; and displaying the hologram in the scene at a third distance from the ER system, the third distance also being an approximation of the first distance based on the new IPD setting, wherein, as a result of displaying the hologram at the third distance, the at least one boundary region of the hologram aligns with the least one boundary region of the object.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Figure 1:
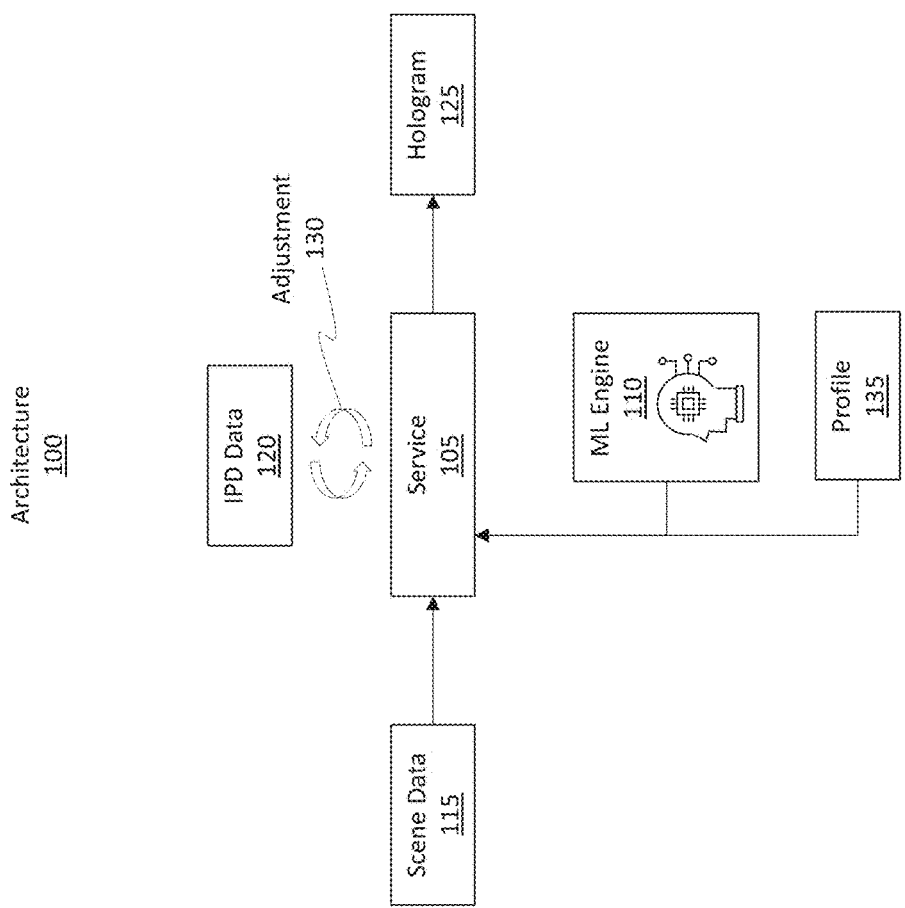
FIG. 1 illustrates an example architecture for calibrating an interpupillary distance (IPD) setting of an extended reality (ER) system.

Stereoscopic rendering, as used in ER devices, exploits a human's visual ability to fuse two different images to thereby give rise to a three-dimensional (3D) perceptual experience. To provide an accurate and comfortable user experience, the user's interpupillary distance (IPD) should match the interocular distance (IOD) of the ER system's displays, where the IOD refers to the distance between the two rendering cameras. Matching the user's IPD to the system's IOD has a significant impact on the user's comfort when operating the ER system.

There are situations, however, when the IPD for a user does not match the system's IOD. As one example, there may be situations where an ER system's eye tracking unit is not sufficiently accurate to determine the user's IPD. As another example, there may be situations where the ER system does not include any type of eye tracking unit. As yet another example, there may be situations where the ER system's eye tracking unit is turned off. In such scenarios, the ER system may not be able to determine the user's IPD and may not be able to adjust its rendering based on the user's specific IPD. Deviations even as small as 2 millimeters (mm) between the user's actual IPD and the ER system's current IPD setting can result in significant discomfort for the user.

The disclosed embodiments present various benefits, advantages, and practical applications to the technical field of rendering virtual imagery. In particular, the disclosed embodiments are directed to a user-in-the-loop solution that allows the ER system to adjust its IPD setting with great precision. Often, the embodiments are practiced in a scenario where the ER system either omits an eye tracking unit or, alternatively, the ER system includes the eye tracking unit, but the eye tracking unit is not operating.

To achieve these benefits, the embodiments identify a physical object. This identification process includes determining the distance the physical object is with respect to the ER system. Optionally, the size of the physical object is determined. The embodiments then generate a hologram, which will be used to calibrate the ER system's IPD setting based on the user's actual IPD. In some scenarios, the hologram is designed to have one or more parameters (e.g., size, visual appearance, and spatial frequency) that are the same as the parameters of the physical object.

The embodiments then display the hologram in the scene. If the ER system's IPD setting matches the user's actual IPD, then the hologram should show a full spatial overlap with the physical object. Stated differently, the hologram should match the physical object precisely. On the other hand, if the ER system's IPD setting does not match the user's actual IPD, then the hologram will be displayed at a depth that is different than the depth of the physical object. For example, the hologram will be displayed in front of the physical object or behind it.

In some embodiments, the embodiments use various criteria in determining which physical object to use as a part of the calibration process. As one example, some embodiments select a physical object that is about 1 diopter (DPT) away from the ER system, thereby ensuring that deviations in vergence are visible with respect to the physical plane. Other criteria may also be used, as will be described in more detail later.

By performing these various operations, the embodiments are able to calibrate an ER system's IPD setting to match the user's actual IPD. Doing so significantly improves the user's experience with the ER system. Such operations will also improve the image rendering processes for the ER system. Accordingly, these and numerous other benefits will now be discussed in more detail throughout the remaining portions of this disclosure.

Example Architectures

Attention will now be directed to FIG. 1, which illustrates an example computing architecture 100. Architecture 100 can, for example, be implemented by an ER system, which includes a head mounted device (HMD). As used herein, the phrases ER system and HMD can be used interchangeably and generally refer to a type of system that allows a user to see various portions of the real world and that also displays virtualized content in the form of holograms. It is typically the case that architecture 100 is implemented on an MR or AR system, or rather, a system that provides passthrough imagery to a user. As used herein, the term "passthrough" refers to a system that allows the user to see at least a portion of the real world.

Architecture 100 is shown as including a service 105. As used herein, the term "service" refers to an automated program that is tasked with performing different actions based on input. In some cases, service 105 can be a deterministic service that operates fully given a set of inputs and without a randomization factor. In other cases, service 105 can be or can include a machine learning (ML) or artificial intelligence engine, as shown by ML engine 110. The ML engine 110 enables service 105 to operate even when faced with a randomization factor.

As used herein, reference to any type of machine learning or artificial intelligence may include any type of machine learning algorithm or device, convolutional neural network(s), multilayer neural network(s), recursive neural network(s), deep neural network(s), decision tree model(s) (e.g., decision trees, random forests, and gradient boosted trees) linear regression model(s), logistic regression model(s), support vector machine(s) ("SVM"), artificial intelligence device(s), or any other type of intelligent computing system. Any amount of training data may be used (and perhaps later refined) to train the machine learning algorithm to dynamically perform the disclosed operations.

In some implementations, service 105 is a cloud service operating in a cloud environment. In some implementations, service 105 is a local service operating on a local device, such as the ER system. In some implementations, service 105 is a hybrid service that includes a cloud component operating in the cloud and a local component operating on a local device. These two components can communicate with one another.

Service 105 is generally tasked with obtaining, accessing, or otherwise determining scene data 115. As used herein, the term "scene" refers to the environment in which the HMD hosting service 105 is operating. A scene can include real-world objects as well as holograms.

Figure 2:
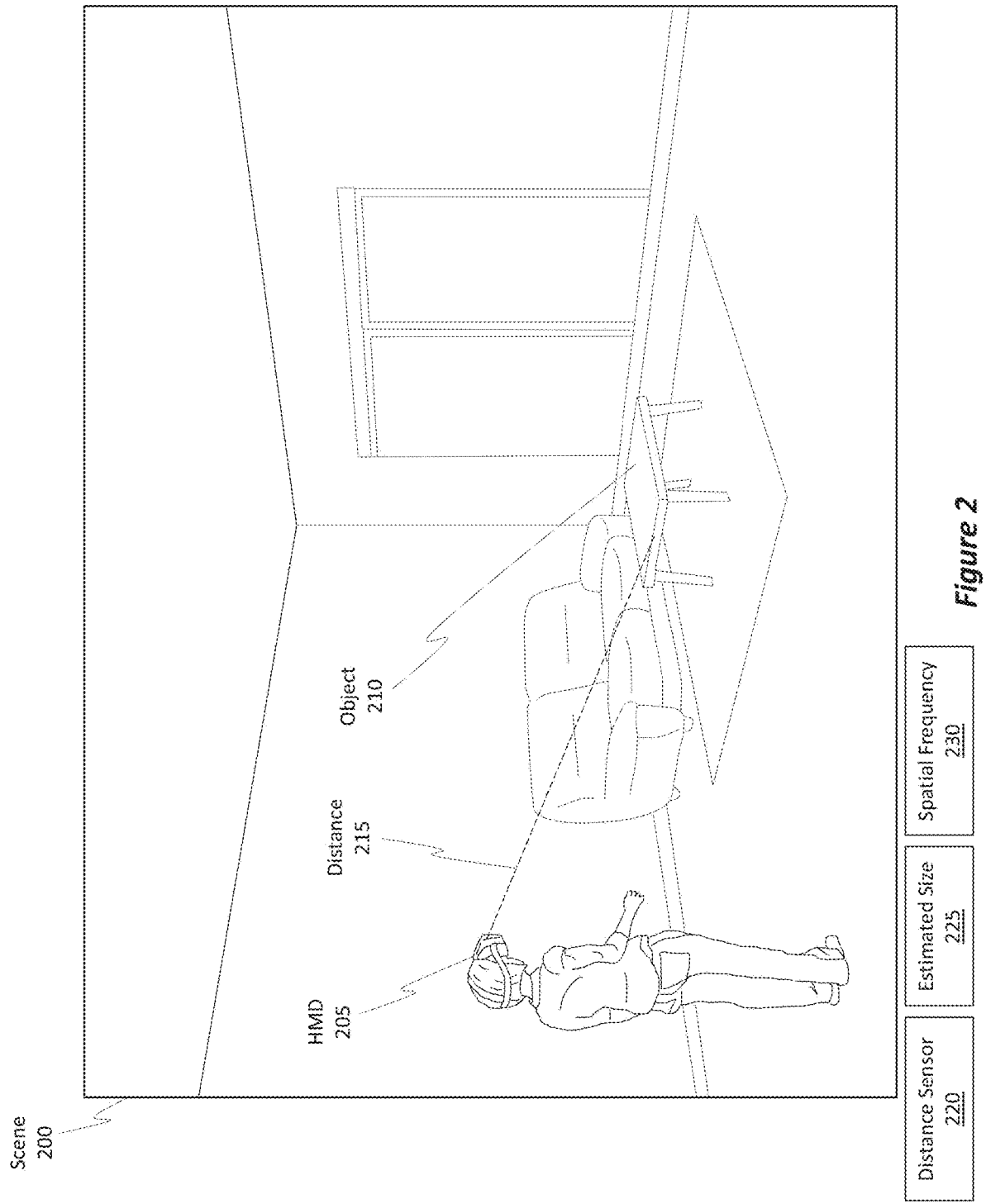
FIG. 2 illustrates an example scene in which an ER system is operating.

Scene data 115 may include any information with respect to the scene. Such information includes, but certainly is not limited to, recognition data for objects in the scene, depth data for those objects, surface reconstruction mapping data for the scene, environmental conditions (e.g., light levels), and so on. Turning briefly to FIG. 2, an example is provided.

FIG. 2 shows a scene 200 in which a user is wearing an HMD 205. HMD 205 can implement service 105 from FIG. 1. Scene 200 includes various objects, such as the table that is labeled as object 210.

Scene data 115 from FIG. 1 can include various information about scene 200, including the objects therein. For instance, scene data 115 can include information about object 210, such as what it is or what type of object it is (e.g., it is a table). Scene data 115 can further include positional information of object 210, such as the distance 215 between HMD 205 and object 210.

Distance 215 can be determined in various different ways. In one example scenario, distance 215 is determined using a distance sensor 220. Distance sensor 220 may include any type of distance determining sensor. Examples of such a sensor include, but are not limited to, any type of infrared sensor (e.g., a time of flight sensor), ultrasonic sensor, image-based sensor (e.g., a stereoscopic image unit that determines distance based on differences in pixel coordinates from two different images), or any other type of distance sensor.

In some cases, distance 215 is an estimated distance. For instance, if HMD 205 analyzes object 210 and is able to determine its characteristics (e.g., such as perhaps by performing an Internet query to determine an identified object's dimensions), then HMD 205 can determine the distance 215 based on how scaled or skewed object 210 appears in an image relative to its known characteristics.

As a specific example, consider an object that has standardized dimensions, such as a dollar bill (or any other currency) or a wall outlet. The dimensions of these objects can be readily queried. An image of those objects in the scene can then be obtained. The object is recognized within the image. Based on the detected size and skew of the object as it appears in the image, the embodiments can determine how far apart HMD 205 is relative to that object. Thus, some embodiments determine distance 215 based on an estimated size 225 or a known size of a recognized object.

Figure 3:
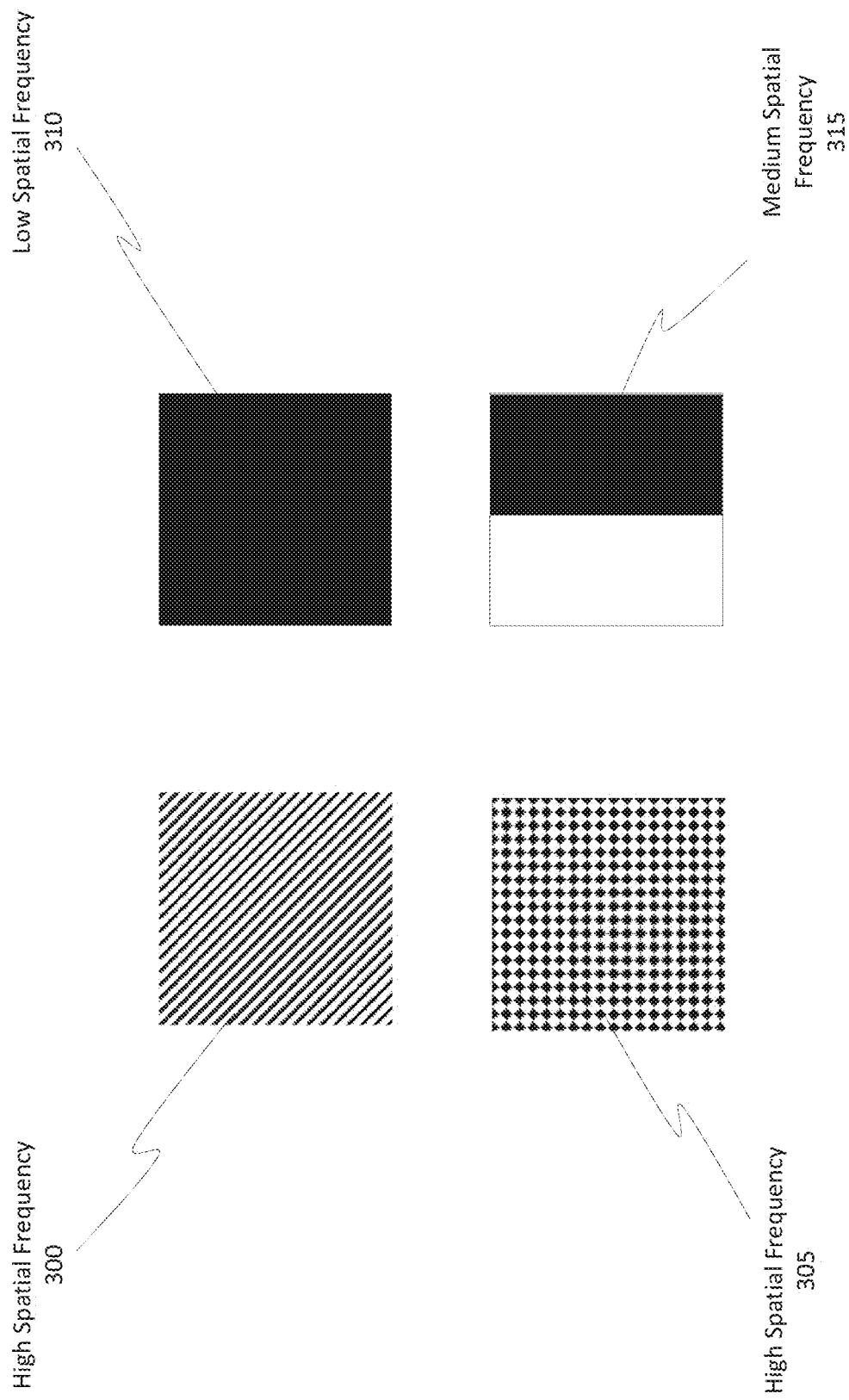
FIG. 3 illustrates examples of spatial frequency.

Scene data 115 also includes information about an object's spatial frequency 230. As used herein, spatial frequency generally refers to how much change in irradiance an object has. FIG. 3 is representative.

FIG. 3 shows four separate images. Two of the images have high irradiance characteristics (i.e. their pixel intensities vary significantly across the entire the image), as shown by high spatial frequency 300 and 305. One image has a medium level of irradiance, as shown by medium spatial frequency 315. One image has a low level of irradiance, as shown by low spatial frequency 310.

Returning to FIG. 2, scene data 115 includes information tracking the spatial frequency 230 for the various objects in the scene. Other characteristics can be included in the scene data 115, such as visual characteristics, depth characteristics, and perhaps even thermal characteristics.

Returning to FIG. 1, service 105 is able to access scene data 115 for a given scene. Service 105 also accesses interpupillary distance (IPD) data 120. IPD data 120 refers to a setting of service 105 that supposedly corresponds to the distance between a user's pupils. It should be noted how, if the IPD data 120 (i.e. an IPD setting of the HMD) is inaccurate with respect to the user's actual IPD, then holograms generated by service 105 (e.g., hologram 125) will be displayed at an incorrect depth. Therefore, in accordance with the disclosed principles, service 105 provides a calibration mechanism to dynamically adjust (e.g., as shown by adjustment 130) the IPD data 120 (i.e. the IPD setting of the HMD) for any given user so that accurate IPD data 120 is used by the HMD and service 105. The adjusted IPD data 120 may then be stored in a profile 135 for a given user so that the correct IPD data can be used for subsequent display operations facilitated by service 105. The remaining figures provide various examples of how this adjustment can be facilitated.

Dynamic Adjustment Of IPD Data To Match Interocular Distance

Figure 4:
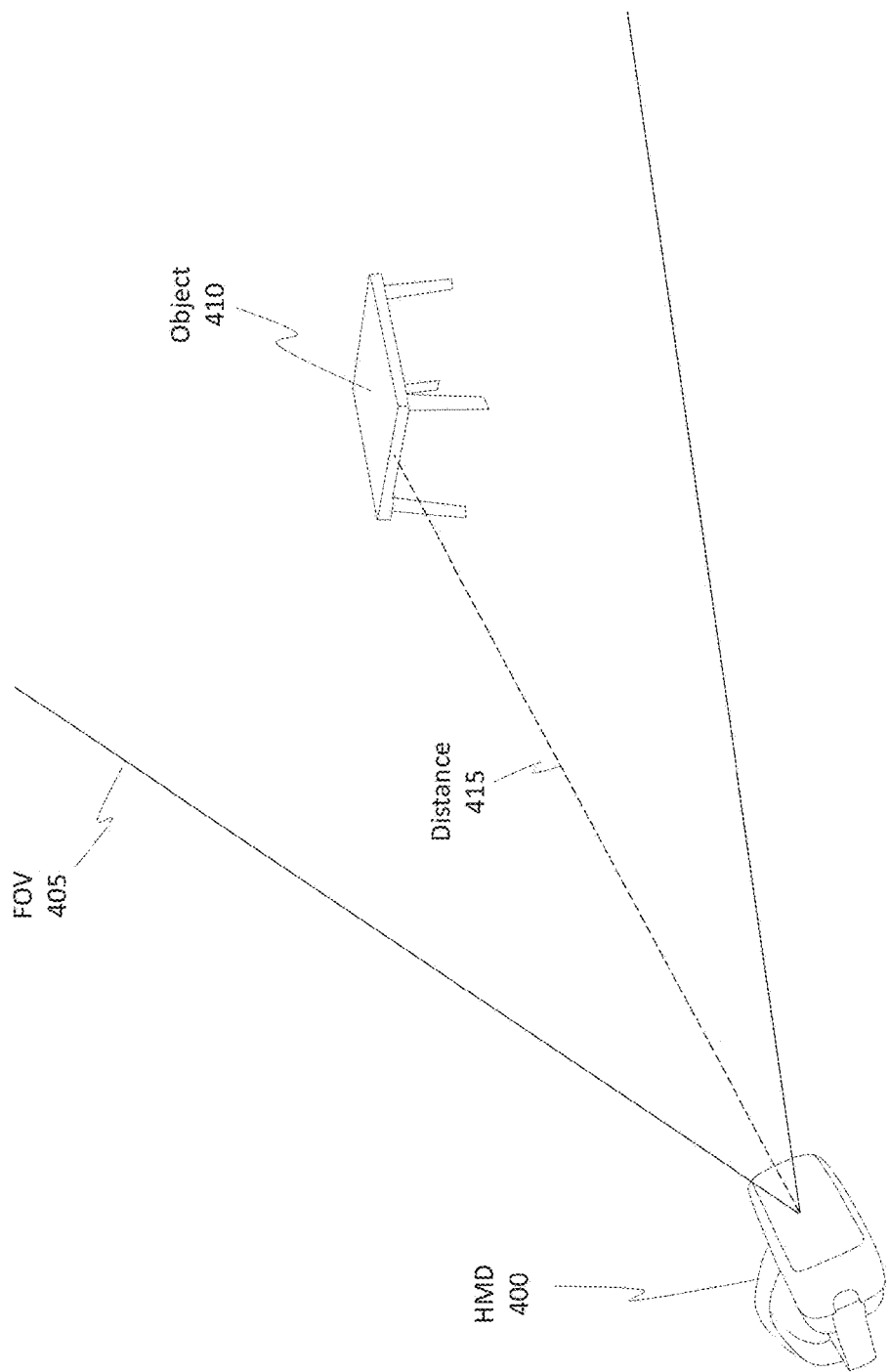
FIG. 4 illustrates an example of an object that is within the field of view (FOV) of an ER system.

FIG. 4 illustrates an HMD 400, which is representative of HMD 205 from FIG. 2 and which can implement service 105 from FIG. 1. FIG. 4 also shows a field of view (FOV) 405 for HMD 400 as well as an object 410 that is included in the FOV 405. A distance 415 exists between HMD 400 and object 410, similar to distance 215 from FIG. 2. Distance 415 can be determined in any of the ways mentioned earlier.

Some embodiments rely on a set of selection criteria when determining what physical object in the scene to use as a part of the calibration process. For instance, some embodiments require the size of the object to consume a threshold amount of the HMD's FOV 405. As various examples, the size of the object may be required to be of a size such that it occupies between about 2 degrees of viewing angle up to about 40 degrees of viewing angle. In some cases, the range may be between about 3-6 degrees of viewing angle. In some cases, the preferred size is such that the object occupies around 10 degrees of viewing angle. As shown by this passage, various ranges can be used. Selecting an object that meets this criteria can help minimize the viewer eye movements required to align the virtual object (i.e. hologram) with the physical object.

In some cases, the embodiments select an object that is within a threshold distance away from the HMD. As an example, the embodiments may select an object that is anywhere from about 0.5 meters to about 3 meters away from the HMD.

Figure 5:
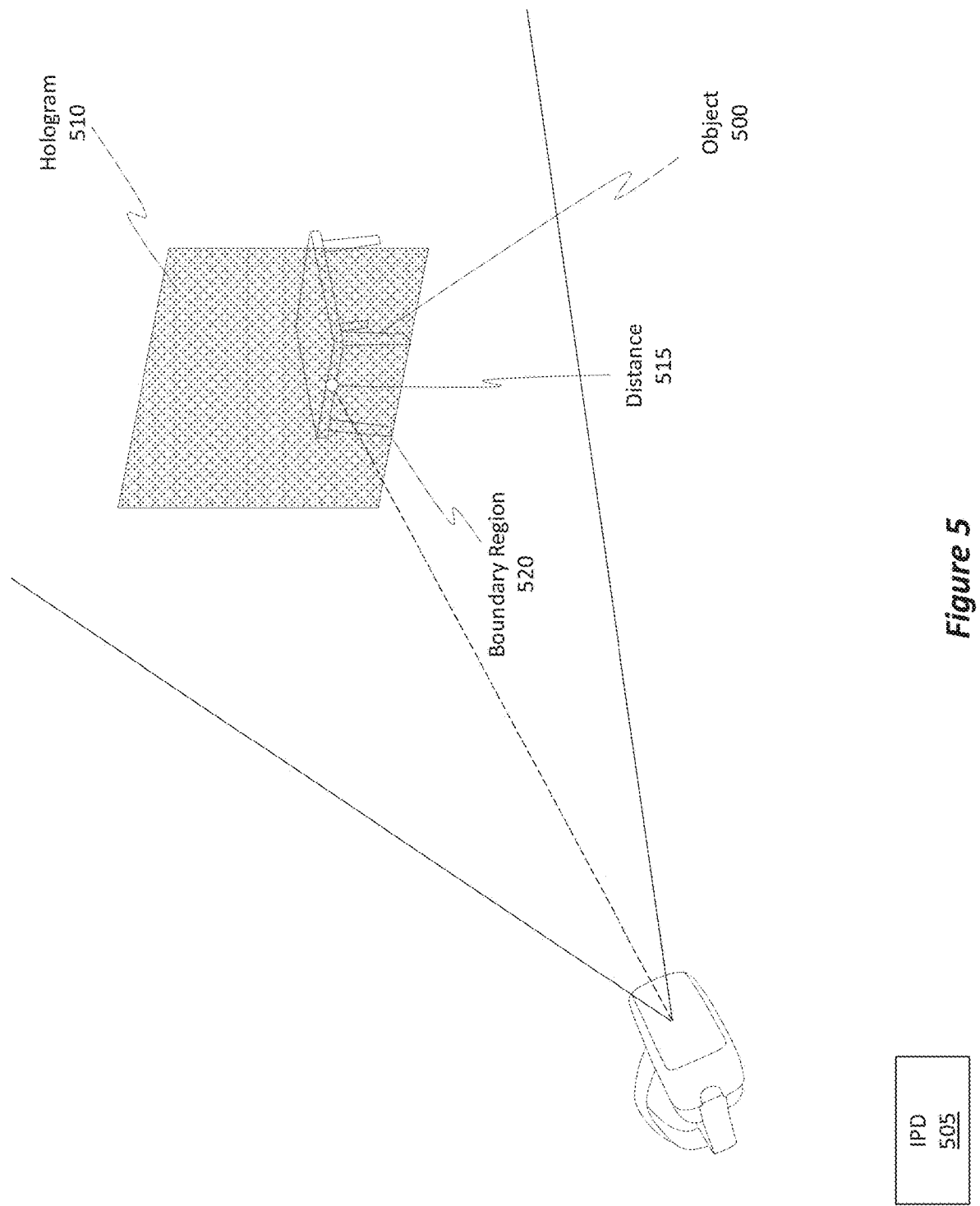
FIG. 5 illustrates how, if the IPD setting of the ER system is correct for the current user, then a hologram will be displayed at a correct depth.

FIG. 5 shows a scenario involving an object 500 that is representative of object 410 from FIG. 4. One objective of the HMD is to display holograms at proper depths. For instance, suppose the current objective of the HMD was to display a hologram right at the edge of object 500. Assuming a correct IPD 505 setting for a user was being used by the HMD, the resulting hologram 510 would be displayed at distance 515, which is the same distance as where the object 500 is relative to the HMD. Consequently, a boundary region 520 of the hologram 510 would align with a boundary region of the object 500. If, however, the IPD 505 setting of the HMD was not correct for the current user, then the hologram 510 would be displayed at a different depth, as shown by FIG. 6.

Figure 6:
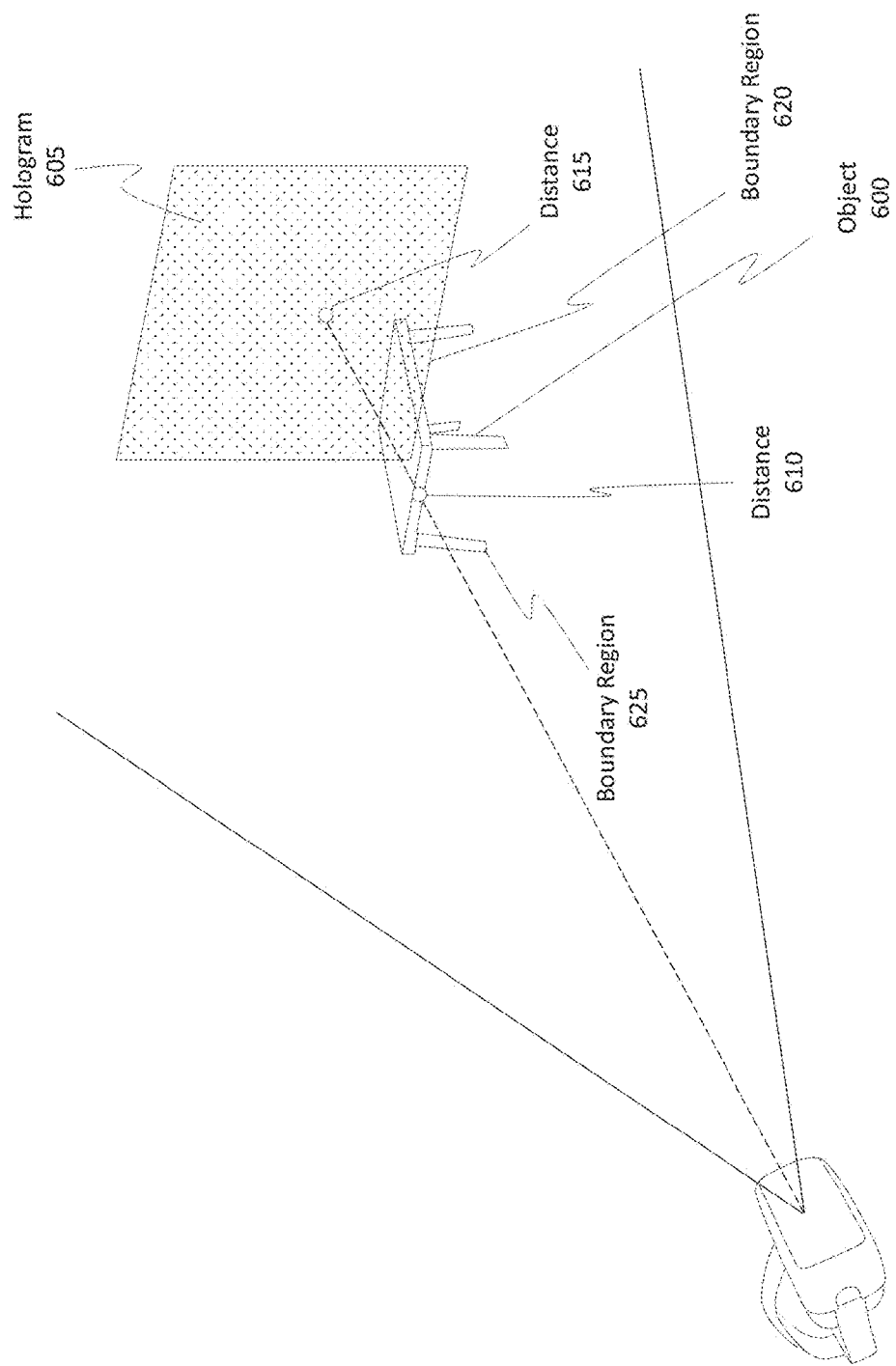
FIG. 6 illustrates an example where the IPD setting is not correct.

FIG. 6 shows an example scenario where an incorrect IPD setting is being used by the HMD, resulting in a hologram being displayed at an incorrect depth. In particular, FIG. 6 shows an object 600 and a hologram 605. Object 600 is a distance 610 away from the HMD. If the correct IPD setting were being used, then the hologram 605 would also be displayed at the same distance 610. Instead, however, hologram 605 is shown as being displayed at distance 615, which is behind object 600. Notice, the boundary region 620 of the hologram 605 does not align with the boundary region 625 of the object 600.

Figure 7:
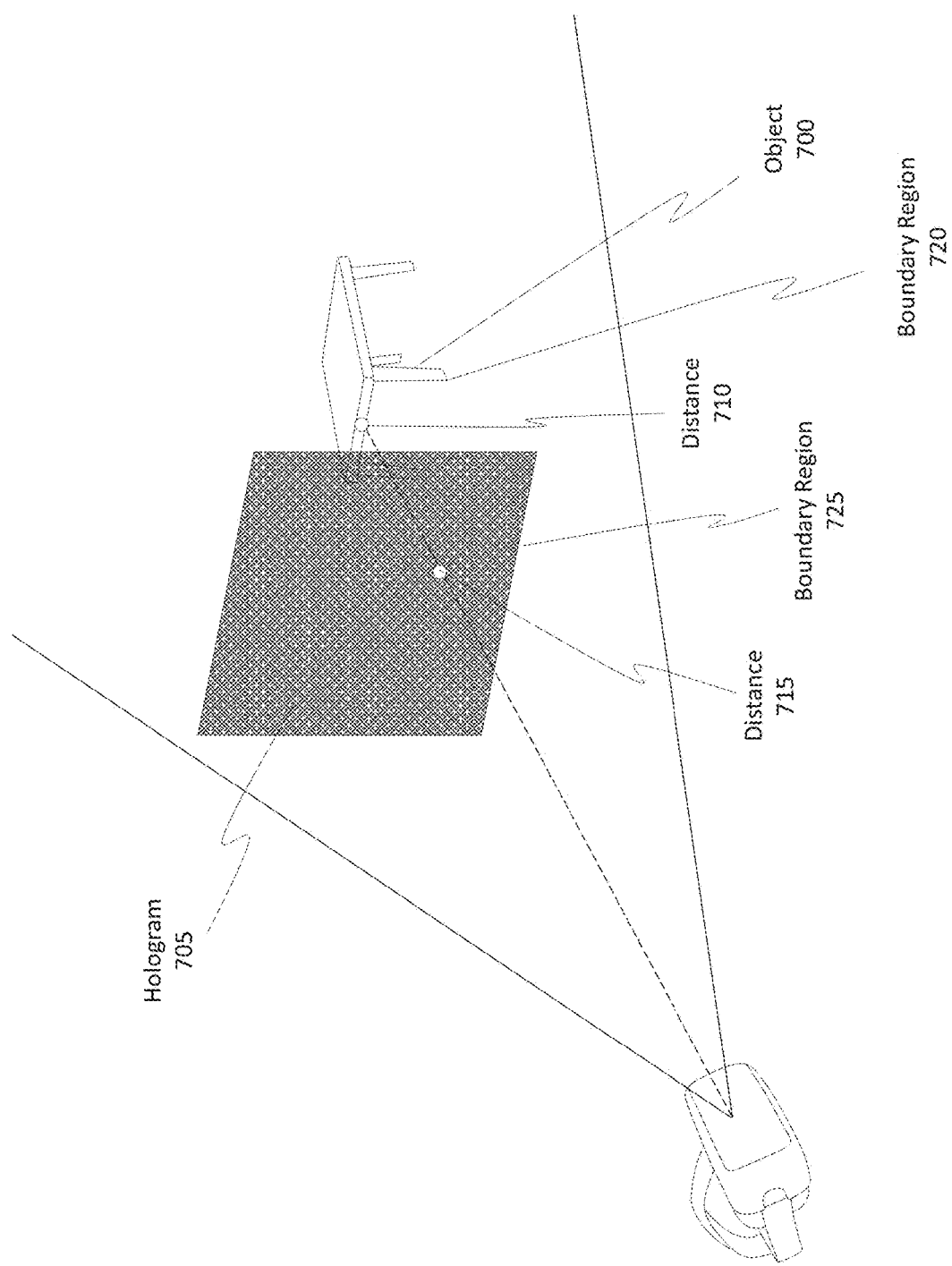
FIG. 7 illustrates another example where the IPD setting is not correct.

FIG. 7 shows another example scenario in which an incorrect IPD setting is being used by the HMD. In particular, FIG. 7 shows an object 700 and a hologram 705. Object 700 is a distance 710 away from the HMD. Because the wrong IPD setting is being used by the HMD, hologram 705, which should be displayed at distance 710, is actually displayed at distance 715. Notice, the boundary region 725 of the hologram 705 does not align with the boundary region 720 of the object.

Figure 8:
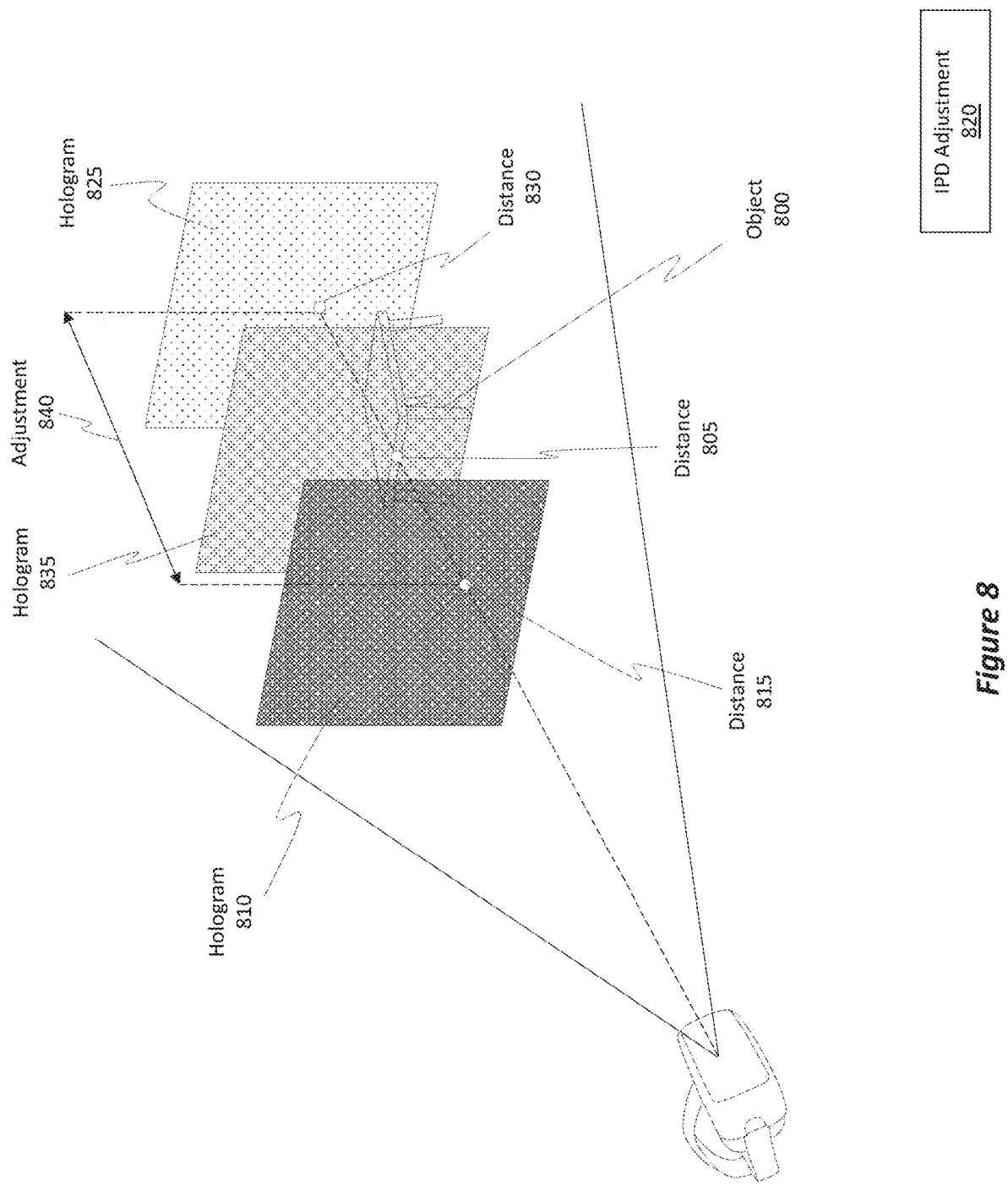
FIG. 8 illustrates an adjustment technique for dynamically adjusting the ER system's IPD setting so that holograms are displayed at the correct depth based on the user's particular IPD characteristics.

The disclosed embodiments are designed to resolve the issues that were described in FIGS. 6 and 7. In particular, the disclosed embodiments present various techniques for dynamically modifying an IPD setting of the HMD in order to calibrate the HMD's IPD setting to a specific user's IPD. FIG. 8 is illustrative.

FIG. 8 shows a scene comprising an object 800. In accordance with the disclosed principles, the embodiments are able to determine a distance 805 between the HMD and the object 800. Optionally, the embodiments also determine a size, shape, texture, and/or type of the object 800.

The embodiments also generate a hologram 810 that corresponds to the object 800. This correspondence can be based on any factor. As one example, at least one boundary region of the hologram 810 can correspond to at least boundary region of the object 800. For instance, the bottom portion of the hologram 810 is shown as being a line, and this line "corresponds" to the line-like region of the leg of object 800.

In some more complicated implementations, the structure of hologram 810 can be designed to match the structure of object 800. For example, hologram 810 can be structured as a table that has the same dimensions as object 800. Further details and examples of this structuring aspect will be provided later. In any event, however, at least one boundary region of hologram 810 corresponds, matches, mimics, or otherwise is associated with at least one boundary region of object 800.

In this example scenario, the HMD is using an incorrect IPD setting for the user currently wearing the HMD. As a result, hologram 810 is displayed at an incorrect distance 815, which is shorter than the accurate distance 805. Notably, if a correct IPD setting were being used, hologram 810 would actually be displayed at distance 805 instead of distance 815.

In accordance with the disclosed principles, the embodiments provide an IPD adjustment 820 mechanism to allow a user to finely tune or calibrate the HMD's IPD setting to correspond to the user's actual IPD or interocular distance. This IPD adjustment 820 mechanism can include any type of adjustment unit or mechanism.

For instance, the IPD adjustment 820 mechanism can include a radial dial on the HMD which the user can rotate clockwise or counterclockwise. Doing so increases or decreases the HMD's IPD setting. The IPD adjustment 820 mechanism can also be implemented via other input techniques, such as touch input with respect to a user interface or hologram, voice input, or any other technique for providing input.

The user is able to adjust the HMD's IPD setting until the hologram aligns with the object. In FIG. 8, the user initially over-adjusted the hologram to a position behind the object 800, as shown by hologram 825 now located at distance 830, which is farther than distance 805.

Further adjustments cause the hologram 835 to finally be positioned at distance 805. Accordingly, the user is able to make various adjustments to an HMD's IPD setting, as shown by adjustment 840. The result of adjusting the IPD setting is that holograms will be displayed at different depths. In accordance with the disclosed principles, the embodiments are able to facilitate a calibration event where a hologram is displayed and where the user can dynamically adjust the HMD's IPD setting until at least one boundary region of the hologram aligns with at least one boundary region of an object whose distance from the HMD is determined.

The embodiments allow the user to adjust the location of the hologram (e.g., up/down/left/right by modifying the IPD setting of the HMD) to fully match the physical object. This calibration process is performed binocularly (i.e. using both eyes). Once the user finalizes his/her IPD setting, the embodiments record the IPD setting, which is then subsequently used as an input for the ER system when displaying holograms.

In some scenarios, multiple calibration events are performed to select an IPD setting for the HMD. The final IPD setting may optionally then be based on an average value for the multiple settings. For instance, during a first time period, the embodiments may perform a calibration event to generate a first IPD setting. During a second time period, the embodiments may perform a second calibration event to generate a second IPD setting. A third IPD setting may subsequently be determined. The final IPD setting can then be based on an averaging of these three calibration events.

As mentioned earlier, some embodiments are selective in which objects are used during the calibration event. For instance, the embodiments may select an object whose spatial frequency satisfies a minimum spatial frequency threshold. Furthermore, some embodiments select objects whose distance from the HMD is within a permissible distance range. For example, the embodiments may select objects that are between about 0.5 meters from the HMD up to about 3 meters from the HMD. Of course, that range can also be modified. For instance, the range can be between about 1 meter and about 2 meters. Some embodiments select objects that have a characteristic that can be determined by the HMD, such as a standardized or known characteristic (e.g., size, shape, texture, etc.).

Figure 9:
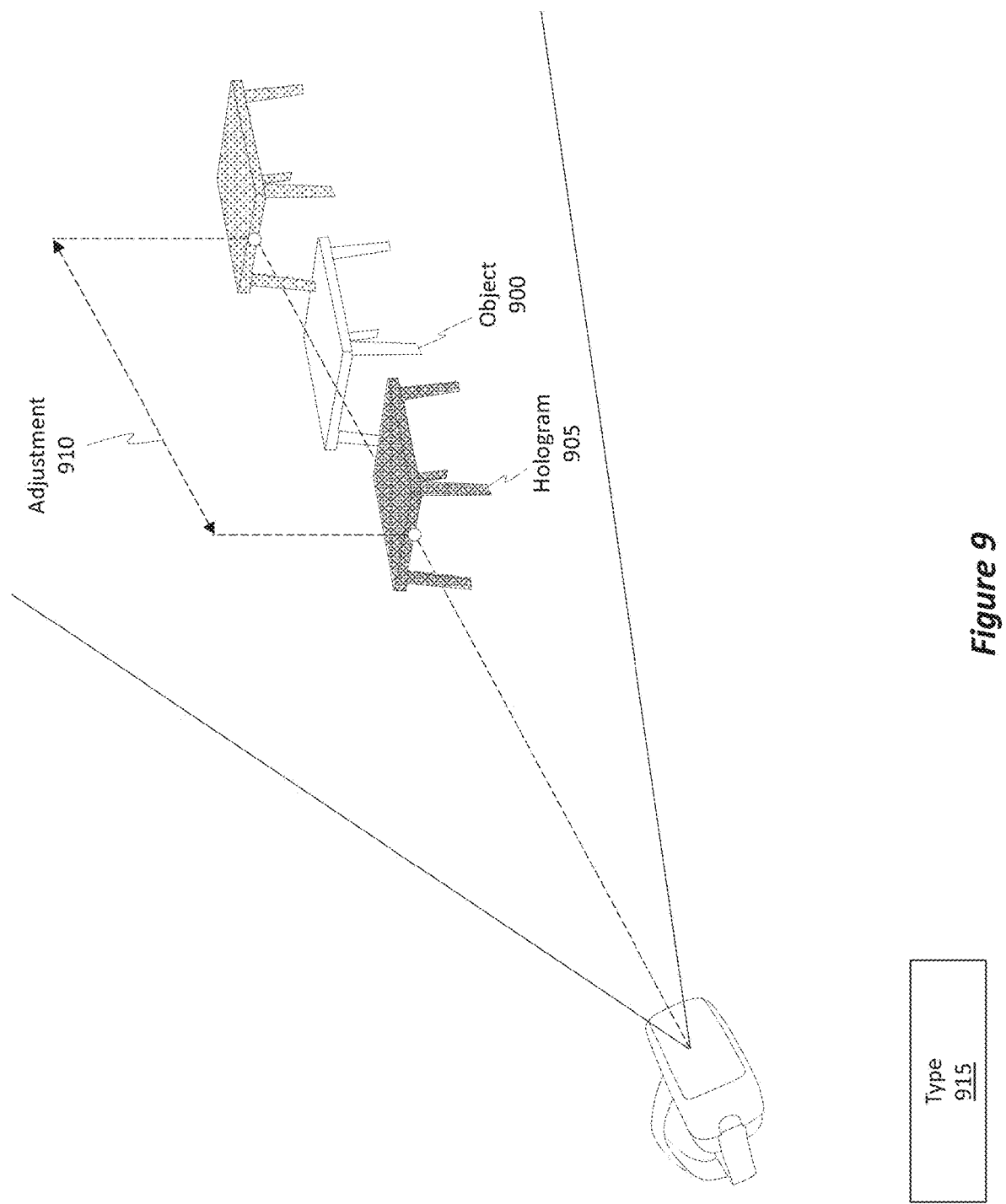
FIG. 9 illustrates how different types of holograms can be used during the adjustment process.

Also, in some embodiments, the hologram is structured in a manner so as to represent the object against which it is being compared. FIG. 9 is illustrative.

FIG. 9 shows an object 900 in the form of a table. The embodiments are able to generate a hologram 905 that appears to be similar to the table, as shown. The user can then adjust the HMD's IPD setting to align the hologram table with the real-world table, as shown by adjustment 910. Thus, some embodiments structure the type 915 of the hologram 905 to coincide with the type of the object 900.

Figure 10:
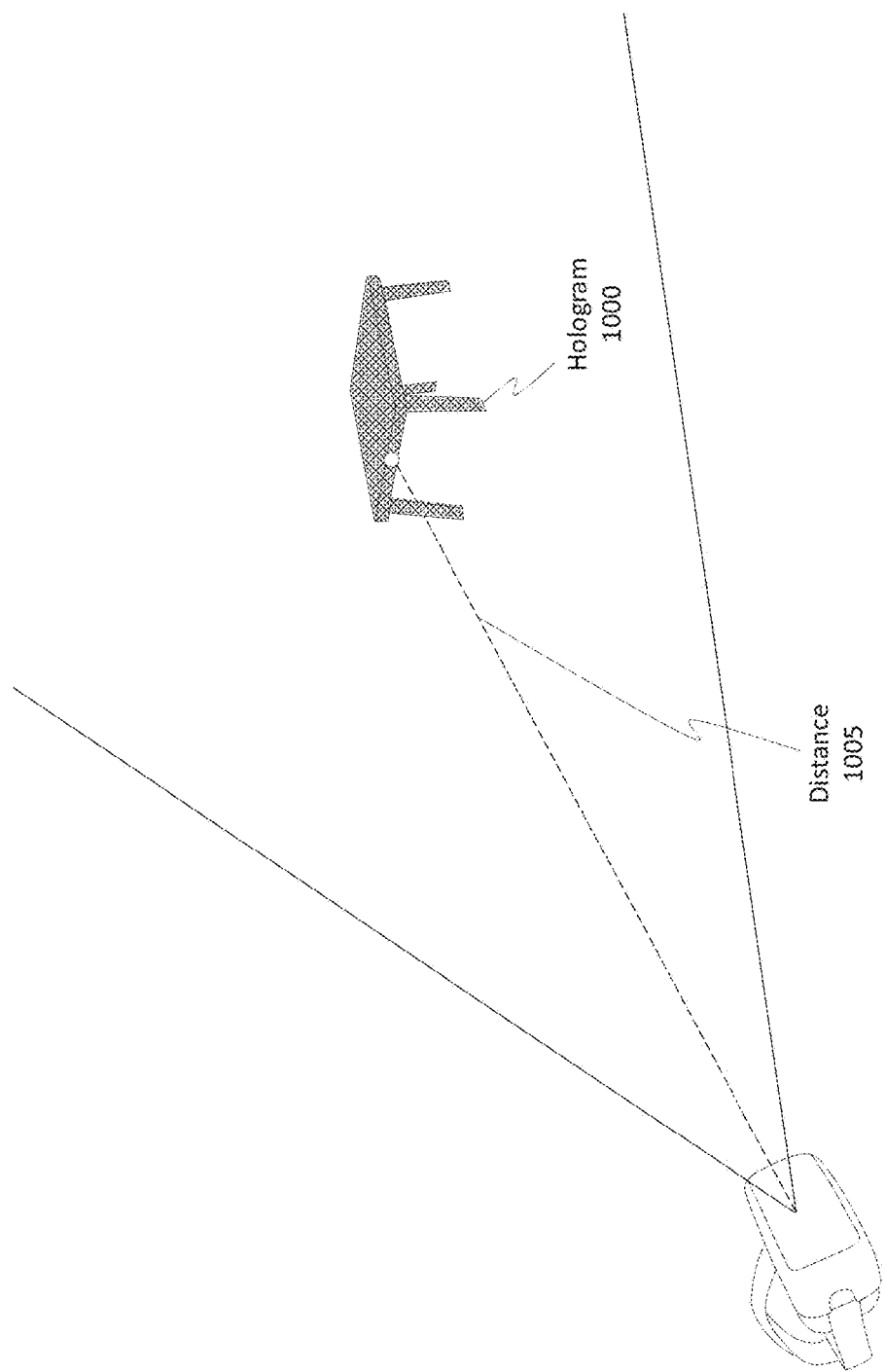
FIG. 10 illustrates a correct depth for a hologram.

FIG. 10 shows the result of calibrating the HMD's IPD setting to the user's actual IPD or interocular distance. In FIG. 10, the hologram 1000 is aligned directly with the underlying object, and the hologram 1000 is displayed at a correct distance 1005, which is the actual distance where the object is located.

By adjusting the IPD setting to coincide with the user's actual IPD, the HMD will be able to subsequently display holograms at their correct positions based on the user's IPD characteristics. The adjusted IPD setting can then be stored in a profile for the user. Subsequent display operations of the ER system can then use the stored IPD setting.

Using Physical Objects With Known Characteristics

Figure 11:
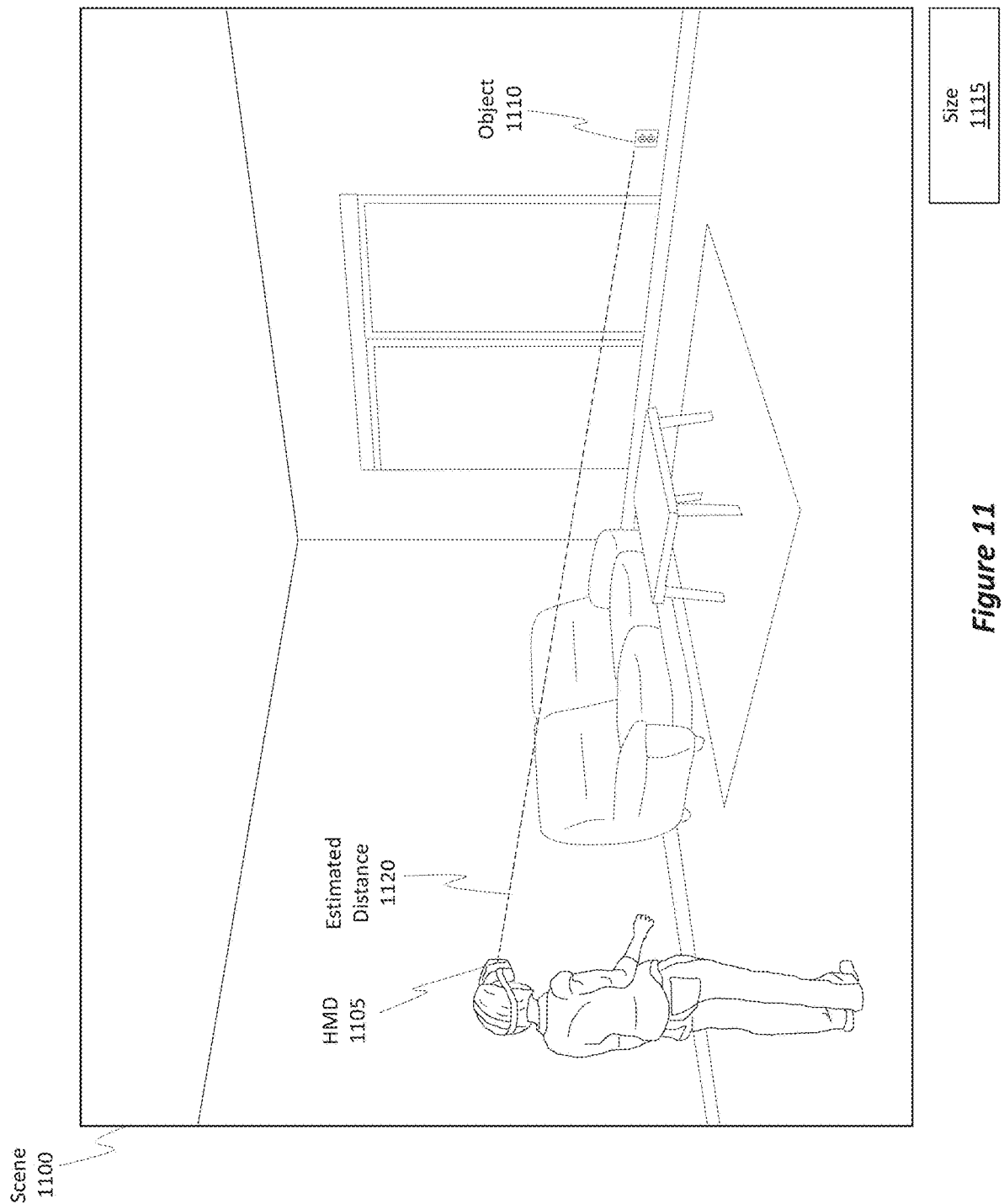
FIG. 11 illustrates another scene that includes an object having known or knowable characteristics.

FIG. 11 shows an example scene 1100 in which a user is wearing an HMD 1105. Scene 1100 includes an object 1110 that has characteristics that can be discovered or that are already known. In this example scenario, object 1110 is an outlet. Outlets have known dimensions.

HMD 1105 is able to generate an image of object 1110, access size 1115 information for the object 1110 (e.g., perhaps by conducting an Internet search), and then generating an estimated distance 1120 from the HMD 1105 to the object 1110 based on the scale and skew characteristics of the object as it is represented in the image. Therefore, in addition to or as an alternative to using a distance sensor, some embodiments are able to estimate the distance based on the size characteristics of an object. In some cases, multiple images or readings can be obtained, and the distance may be based on an aggregation or averaging of the collected data.

Figure 12:
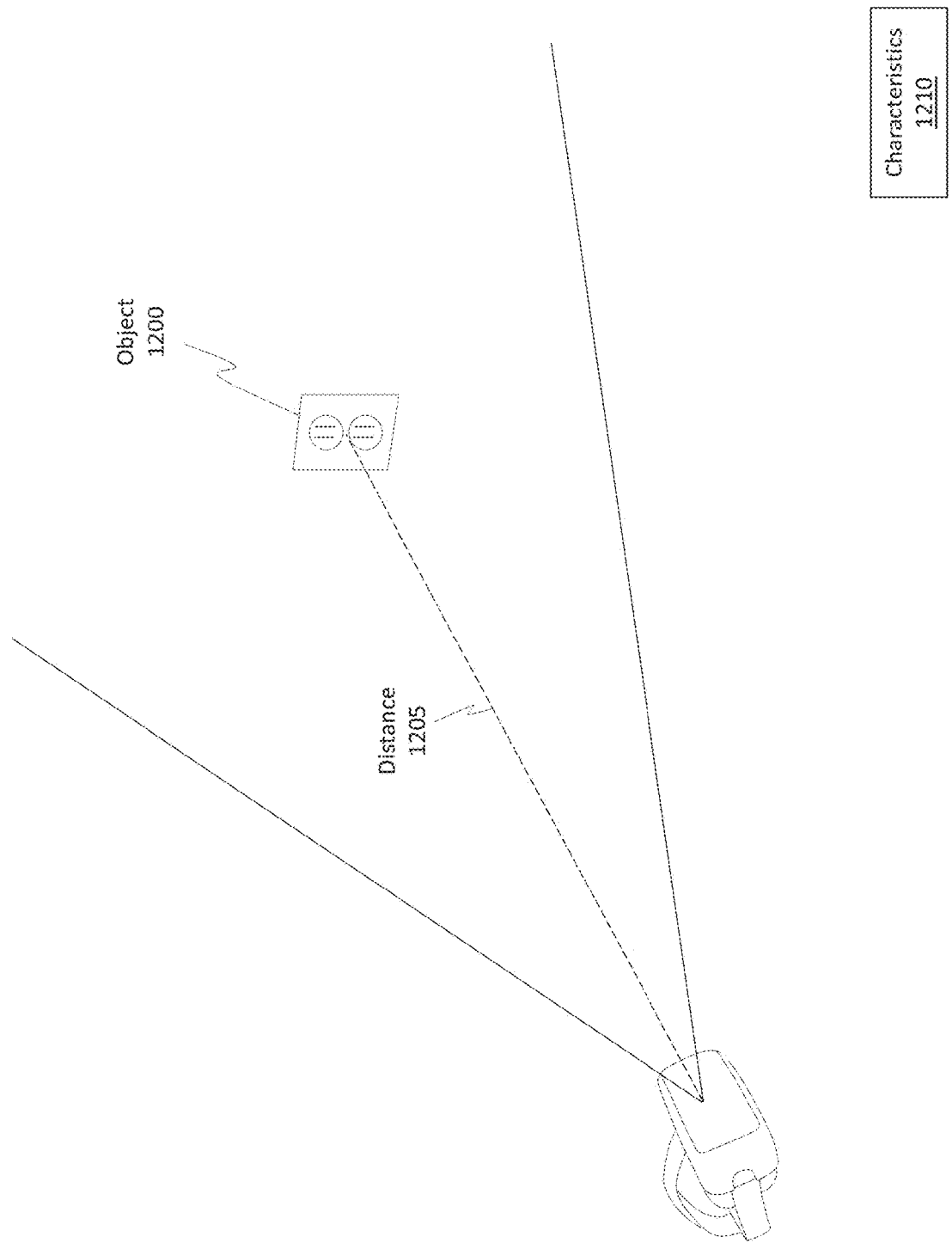
FIG. 12 illustrates the object having known characteristics.

FIG. 12 shows the object 1200. Object 1200 is a distance 1205 away from the HMD. As discussed, object 1200 has known or knowable characteristics 1210.

Figure 13:
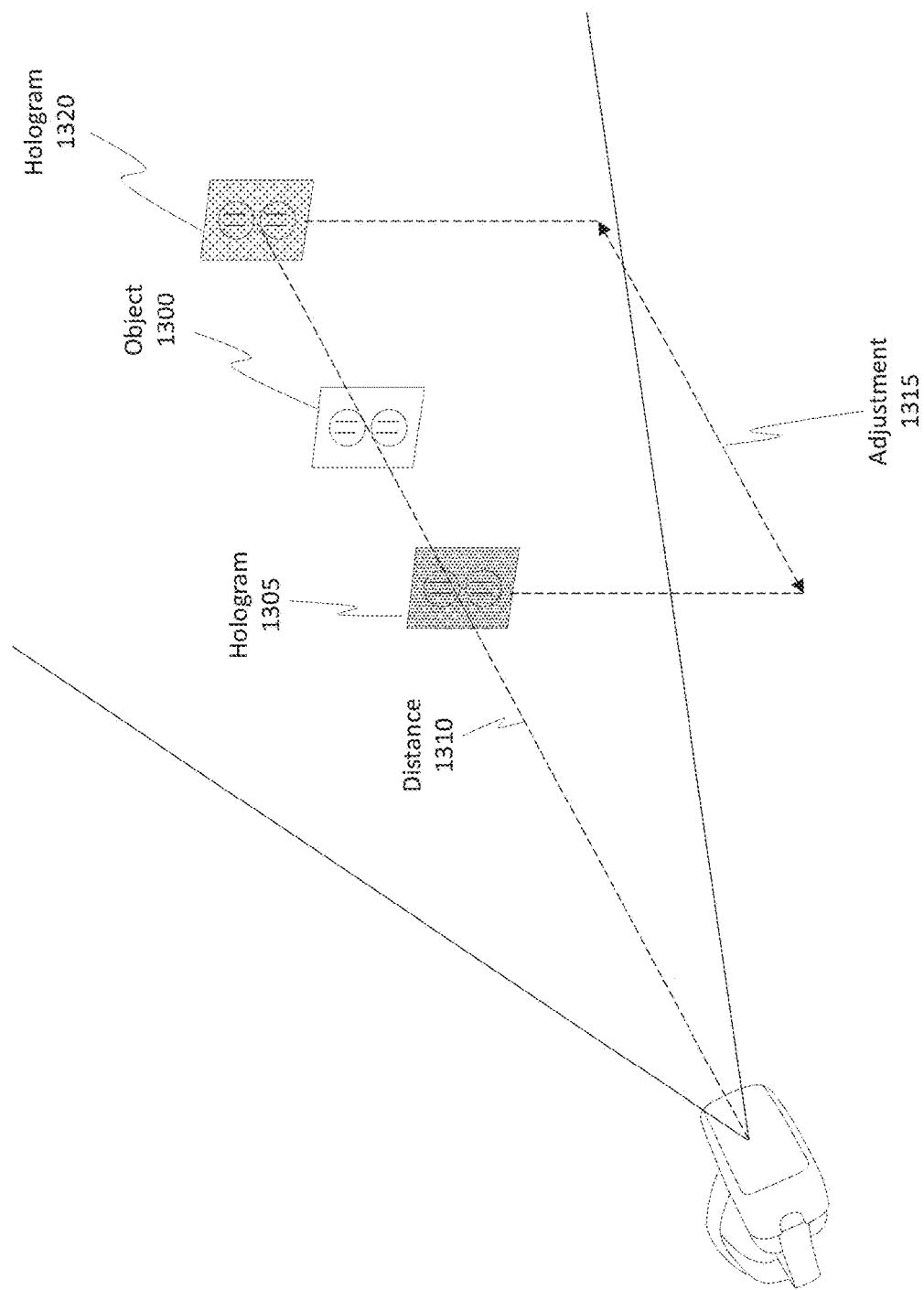
FIG. 13 illustrates another scenario involving the calibration event.

FIG. 13 shows an object 1300 and a hologram 1305. Initially, hologram 1305 is displayed at an incorrect distance 1310 because of the use of an incorrect IPD setting. The user is able to facilitate an adjustment 1315 operation to modify the distance at which the hologram is displayed. In FIG. 13, the user over-adjusted, resulting in the hologram 1320 being displayed at its current position. The user can make further granular adjustments until the hologram is aligned with the underlying object 1300.

Example Methods

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 14:
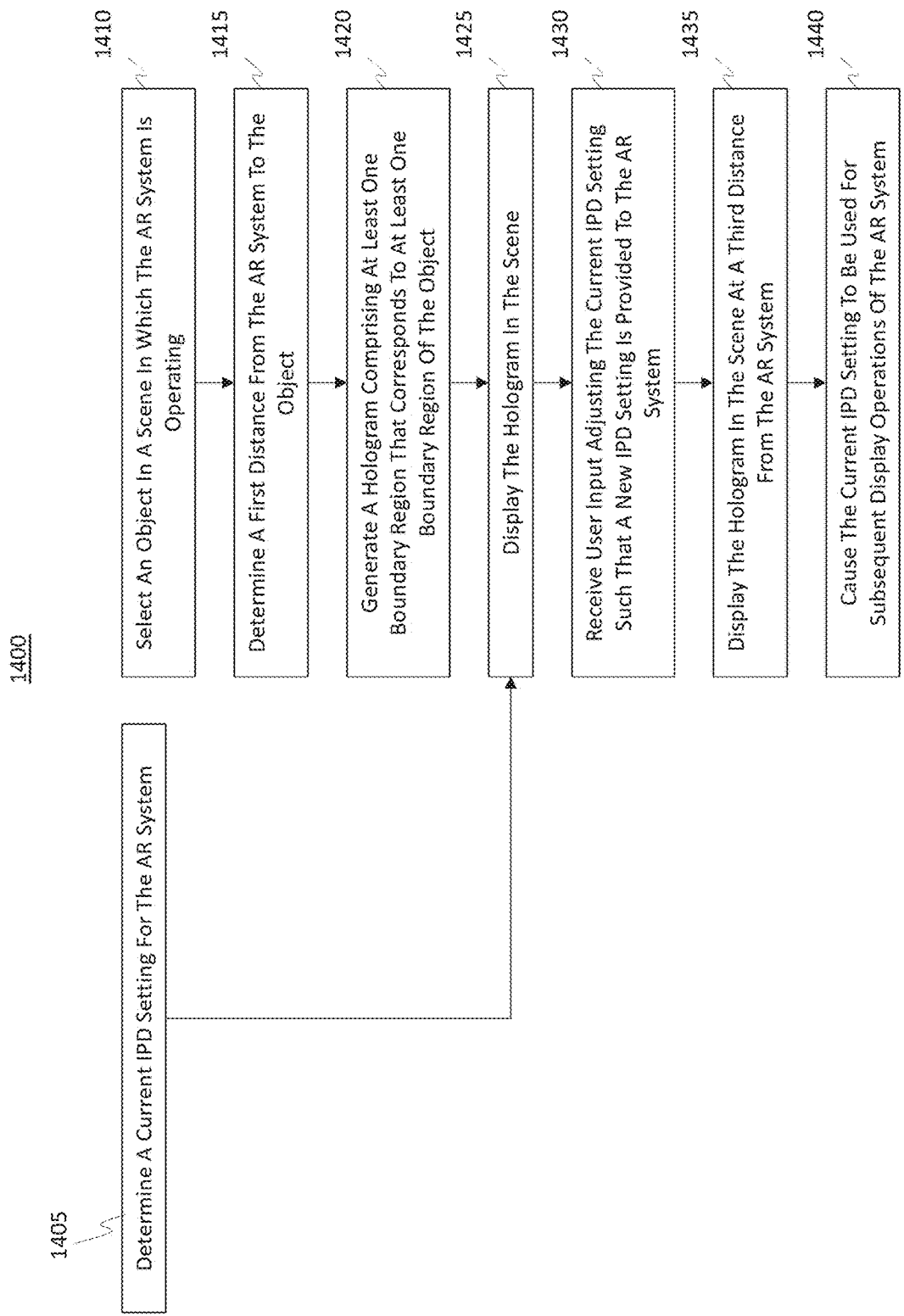
FIG. 14 illustrates a flowchart of an example method for calibrating an ER system's IPD setting.

Attention will now be directed to FIG. 14, which illustrates a flowchart of an example method 1400 for facilitating a calibration of an interpupillary distance (IPD) setting for an ER system. Method 1400 can be implemented by the ER system performing the calibration event. More particularly, method 1400 can be implemented by the service 105 of FIG. 1, where service 105 can be implemented on the ER system.

Method 1400 includes an act (act 1405) of determining a current IPD setting for the ER system. It is typically the case that the ER system either does not include an eye tracking unit or its eye tracking unit is not currently operational.

Asynchronously with act 1405, act 1410 involves selecting an object in a scene in which the ER system is operating. Optionally, the object is selected based on a determination that a spatial frequency of the object satisfies a spatial frequency threshold. Other selection criteria can also be used, as mentioned earlier.

Act 1415 includes determining a first distance from the ER system to the object. In some embodiments, the first distance is an estimated distance. The estimated distance may be based on the size of the object, where the size of the object is a known size based on known characteristics for the object. The embodiments acquire an image of the object within the scene. The image is then analyzed to detect scaling and skew of the object. Based on that scaling and skew, a distance or depth from the ER system to the object can be estimated.

In some implementations, the first distance is determined using a distance sensor comprising one or more of a time-of-flight sensor, a stereoscopic camera pair, or an ultrasonic sensor. Thus, in some cases, the first distance is one of an estimated distance or a determined distance determined using a distance sensor.

Optionally, a size of the object is determined in real-time. This size determination is based on an image of the object, where that image is generated by the ER system. In some cases, the size of the object is determined based on standard data for the object.

Act 1420 includes generating a hologram comprising at least one boundary region that corresponds to at least one boundary region of the object. In some implementations, the hologram is structured to visually mimic the object. For example, if the object is a table or an outlet, then the hologram may be a table or an outlet. Thus, in some embodiments, the hologram is of a same type as a type of the object.

In some cases, the hologram is a simplified hologram, such as one comprising a border corresponding to a border of the object. In some cases, the hologram is a single line or curve, and the line or curve corresponds to a line or curve of the object.

In some cases, the hologram is more complex and includes texture, color, and other image artifacts that are representative of the actual object. For instance, if the object is a painting or picture, then the hologram may be a holographic representation of the painting or picture. Thus, in some cases, the hologram is a complex hologram, such as one that has a spatial frequency that matches (e.g., within a threshold level) a spatial frequency of the object. Stated differently, the spatial frequency of the hologram may, in some cases, be within a threshold level relative to the spatial frequency of the object. In other cases, simplified holograms can be used.

Act 1425 includes displaying the hologram in the scene. The hologram is displayed based on the current IPD setting for the ER system. The hologram is displayed at a second distance from the ER system, where the second distance is observably different than the first distance. To be "observably different," it means the user observes the hologram at a different depth than the object. For example, the second distance is observably shorter or observably longer than the first distance. It can also be said that the second distance is an approximation of the first distance based on the current IPD setting.

Act 1430 includes receiving user input adjusting the current IPD setting of the ER system. As a result, a new IPD setting is provided to the ER system.

Act 1435 includes displaying the hologram in the scene at a third distance from the ER system. The third distance is observably the same as the first distance. To be "observably the same," it means the user observes the hologram as spatially overlapping the physical object, or rather, as being at the same depth as the physical object. It can also be said that the third distance is an approximation of the first distance based on the new IPD setting.

Desirably, the third distance will be the same as the first distance or is at least within a threshold distance relative to the first distance. As a result of displaying the hologram at the third distance, the at least one boundary region of the hologram aligns with the least one boundary region of the object. Based on this alignment, the ER system's IPD setting is now calibrated to the user's actual IPD characteristics.

Act 1440 includes causing the current IPD setting to be used for subsequent display operations of the ER system. A profile for a user who is using the ER system can be accessed or perhaps generated. The new IPD setting can then be stored in the profile for the user. Subsequent display operations of the ER system may then rely on the current IPD setting for this particular user.

Example Computer/Computer Systems

Figure 15:
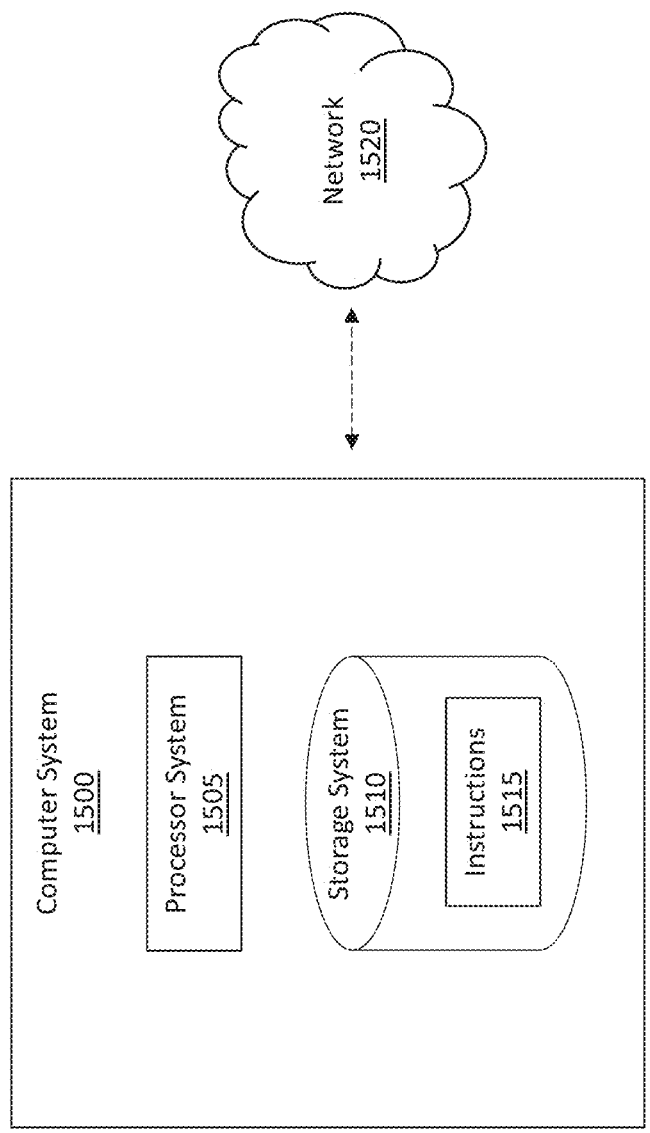
FIG. 15 illustrates an example computer system capable of performing any of the disclosed operations.

Attention will now be directed to FIG. 15 which illustrates an example computer system 1500 that may include and/or be used to perform any of the operations described herein, such as method 1400. Computer system 1500 can also implement service 105 of FIG. 1. Computer system 1500 may take various different forms. For example, computer system 1500 may be embodied as a tablet, a desktop, a laptop, a mobile device, an HMD, or a standalone device, such as those described throughout this disclosure. Computer system 1500 may also be a distributed system that includes one or more connected computing components/devices that are in communication with computer system 1500.

In its most basic configuration, computer system 1500 includes various different components. FIG. 15 shows that computer system 1500 includes a processor system 1505 comprising one or more processor(s) (aka a "hardware processing unit") and a storage system 1510.

Regarding the processor(s) of the processor system 1505, it will be appreciated that the functionality described herein can be performed, at least in part, by one or more hardware logic components. For example, and without limitation, illustrative types of hardware logic components/processors that can be used include Field-Programmable Gate Arrays ("FPGA"), Program-Specific or Application-Specific Integrated Circuits ("ASIC"), Program-Specific Standard Products ("ASSP"), System-On-A-Chip Systems ("SOC"), Complex Programmable Logic Devices ("CPLD"), Central Processing Units ("CPU"), Graphical Processing Units ("GPU"), or any other type of programmable hardware.

As used herein, the terms "executable module," "executable component," "component," "module," "service," or "engine" can refer to hardware processing units or to software objects, routines, or methods that may be executed on computer system 1500. The different components, modules, engines, and services described herein may be implemented as objects or processors that execute on computer system 1500 (e.g. as separate threads).

Storage system 1510 may be physical system memory, which may be volatile, non-volatile, or some combination of the two. The term "memory" may also be used herein to refer to non-volatile mass storage such as physical storage media. If computer system 1500 is distributed, the processing, memory, and/or storage capability may be distributed as well.

Storage system 1510 is shown as including executable instructions 1515. The executable instructions 1515 represent instructions that are executable by the processor(s) of computer system 1500 to perform the disclosed operations, such as those described in the various methods.

The disclosed embodiments may comprise or utilize a special-purpose or general-purpose computer including computer hardware, such as, for example, one or more processors and system memory, as discussed in greater detail below. Embodiments also include physical and other computer-readable media for carrying or storing computer-executable instructions and/or data structures. Such computer-readable media can be any available media that can be accessed by a general-purpose or special-purpose computer system. Computer-readable media that store computer-executable instructions in the form of data are "physical computer storage media" or a "hardware storage device." Furthermore, computer-readable storage media, which includes physical computer storage media and hardware storage devices, exclude signals, carrier waves, and propagating signals. On the other hand, computer-readable media that carry computer-executable instructions are "transmission media" and include signals, carrier waves, and propagating signals. Thus, by way of example and not limitation, the current embodiments can comprise at least two distinctly different kinds of computer-readable media: computer storage media and transmission media.

Computer storage media (aka "hardware storage device") are computer-readable hardware storage devices, such as RAM, ROM, EEPROM, CD-ROM, solid state drives ("SSD") that are based on RAM, Flash memory, phase-change memory ("PCM"), or other types of memory, or other optical disk storage, magnetic disk storage or other magnetic storage devices, or any other medium that can be used to store desired program code means in the form of computer-executable instructions, data, or data structures and that can be accessed by a general-purpose or special-purpose computer.

Computer system 1500 may also be connected (via a wired or wireless connection) to external sensors (e.g., one or more remote cameras) or devices via a network 1520. For example, computer system 1500 can communicate with any number devices or cloud services to obtain or process data. In some cases, network 1520 may itself be a cloud network. Furthermore, computer system 1500 may also be connected through one or more wired or wireless networks to remote/separate computer systems(s) that are configured to perform any of the processing described with regard to computer system 1500.

A "network," like network 1520, is defined as one or more data links and/or data switches that enable the transport of electronic data between computer systems, modules, and/or other electronic devices. When information is transferred, or provided, over a network (either hardwired, wireless, or a combination of hardwired and wireless) to a computer, the computer properly views the connection as a transmission medium. Computer system 1500 will include one or more communication channels that are used to communicate with the network 1520. Transmissions media include a network that can be used to carry data or desired program code means in the form of computer-executable instructions or in the form of data structures. Further, these computer-executable instructions can be accessed by a general-purpose or special-purpose computer. Combinations of the above should also be included within the scope of computer-readable media.

Upon reaching various computer system components, program code means in the form of computer-executable instructions or data structures can be transferred automatically from transmission media to computer storage media (or vice versa). For example, computer-executable instructions or data structures received over a network or data link can be buffered in RAM within a network interface module (e.g., a network interface card or "NIC") and then eventually transferred to computer system RAM and/or to less volatile computer storage media at a computer system. Thus, it should be understood that computer storage media can be included in computer system components that also (or even primarily) utilize transmission media.

Computer-executable (or computer-interpretable) instructions comprise, for example, instructions that cause a general-purpose computer, special-purpose computer, or special-purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the embodiments may be practiced in network computing environments with many types of computer system configurations, including personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The embodiments may also be practiced in distributed system environments where local and remote computer systems that are linked (either by hardwired data links, wireless data links, or by a combination of hardwired and wireless data links) through a network each perform tasks (e.g. cloud computing, cloud services and the like). In a distributed system environment, program modules may be located in both local and remote memory storage devices.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An extended reality (ER) system that facilitates calibration of an interpupillary distance (IPD) setting, said ER system comprising:
   a processor system; and
   a storage system that stores instructions that are executable by the processor system to cause the ER system to:
      determine a current IPD setting for the ER system;
      select an object in a scene in which the ER system is operating;
      determine a first distance from the ER system to the object;
      generate a hologram comprising at least one boundary region that corresponds to at least one boundary region of the object;
      display the hologram in the scene, wherein the hologram is displayed based on the current IPD setting for the ER system, and wherein the hologram is displayed at a second distance from the ER system, the second distance being observably different than the first distance;
      receive user input adjusting the current IPD setting such that a new IPD setting is provided to the ER system;
      display the hologram in the scene at a third distance from the ER system, the third distance being observably the same as the first distance, wherein, as a result of displaying the hologram at the third distance, the at least one boundary region of the hologram aligns with the least one boundary region of the object; and
      cause the current IPD setting to be used for subsequent display operations of the ER system.

2. The ER system of claim 1, wherein the ER system either omits an eye tracking unit or, alternatively, the ER system includes the eye tracking unit, but the eye tracking unit is not operating.

3. The ER system of claim 1, wherein the first distance is an estimated distance, and wherein the estimated distance is based on a size of the object, the size of the object being a known size based on known characteristics for the object.

4. The ER system of claim 1, wherein the first distance is determined using a distance sensor comprising one or more of a time-of-flight sensor, a stereoscopic camera pair, or an ultrasonic sensor.

5. The ER system of claim 1, wherein a size of the object is determined in real-time based on an image of the object, where that image is generated by the ER system.

6. The ER system of claim 1, wherein a size of the object is determined based on standard data for the object.

7. The ER system of claim 1, wherein the object is selected based on a determination that a spatial frequency of the object satisfies a spatial frequency threshold.

8. The ER system of claim 1, wherein the hologram is structured to visually mimic the object.

9. The ER system of claim 1, wherein the hologram is of a same type as a type of the object.

10. The ER system of claim 1, wherein the second distance is observably shorter than the first distance.

11. The ER system of claim 1, wherein the second distance is observably longer than the first distance.

12. The ER system of claim 1, wherein a spatial frequency of the hologram is within a threshold level relative to a spatial frequency of the object.

13. The ER system of claim 1, wherein the hologram is a simplified hologram comprising a border corresponding to a border of the object.

14. A method, implemented by an extended reality (ER) system, for facilitating calibration of an interpupillary distance (IPD) setting for the ER system, said method comprising:
- determining a current IPD setting for the ER system;
- selecting an object in a scene in which the ER system is operating;
- determining a first distance from the ER system to the object;
- generating a hologram that corresponds to the object;
- displaying the hologram in the scene, wherein the hologram is displayed based on the current IPD setting for the ER system, and wherein the hologram is displayed at a second distance from the ER system, the second distance being an approximation of the first distance based on the current IPD setting;
- receiving user input adjusting the current IPD setting such that a new IPD setting is provided to the ER system;
- displaying the hologram in the scene at a third distance from the ER system, the third distance also being an approximation of the first distance based on the new IPD setting; and
- causing the current IPD setting to be used for subsequent display operations of the ER system.

15. The method of claim 14, wherein the method further includes determining a size of the object.

16. The method of claim 14, wherein a profile for a user who is using the ER system is accessed or generated, and wherein the new IPD setting is stored in the profile for the user.

17. The method of claim 14, wherein the hologram is a complex hologram having a spatial frequency that matches, within a threshold level, a spatial frequency of the object.

18. A method, implemented by an extended reality (ER) system, for facilitating calibration of an interpupillary distance (IPD) for the ER system, said method comprising:
- determining a current IPD setting for the ER system;
- selecting an object in a scene in which the ER system is operating;
- determining a first distance from the ER system to the object;
- generating a hologram comprising at least one boundary region that corresponds to at least one boundary region of the object;
- displaying the hologram in the scene, wherein the hologram is displayed based on the current IPD setting for the ER system, and wherein the hologram is displayed at a second distance from the ER system, the second distance being an approximation of the first distance based on the current IPD setting;
- receiving user input adjusting the current IPD setting such that a new IPD setting is provided to the ER system; and
- displaying the hologram in the scene at a third distance from the ER system, the third distance also being an approximation of the first distance based on the new IPD setting, wherein, as a result of displaying the hologram at the third distance, the at least one boundary region of the hologram aligns with the least one boundary region of the object.

19. The method of claim 18, wherein the current IPD setting is stored in a profile for a user wearing the ER system, and wherein subsequent display operations of the ER system rely on the current IPD setting.

20. The method of claim 18, wherein the first distance is one of an estimated distance or a determined distance determined using a distance sensor.

* * * * *